(12) United States Patent
Romang (10) Patent No.: US 11,471,348 B2
(45) Date of Patent: Oct. 18, 2022

(54) RESCUE STRAP FOR CARRYING A PATIENT

(71) Applicant: Timothy M. Romang, Hampton, IL (US)

(72) Inventor: Timothy M. Romang, Hampton, IL (US)

( * ) Notice: Subject to any disclaimer, the term of this patent is extended or adjusted under 35 U.S.C. 154(b) by 0 days.

(21) Appl. No.: 17/167,943

(22) Filed: Feb. 4, 2021

(65) Prior Publication Data

US 2021/0244591 A1    Aug. 12, 2021

Related U.S. Application Data

(60) Provisional application No. 62/972,037, filed on Feb. 9, 2020.

(51) Int. Cl.
*A61G 7/10* (2006.01)
*A61F 5/37* (2006.01)

(52) U.S. Cl.
CPC .......... *A61G 7/1023* (2013.01); *A61F 5/3738* (2013.01)

(58) Field of Classification Search
CPC ... A61G 7/1023; A61G 7/1013; A61F 5/3738; A61F 5/3723
USPC .......................... 5/81.1 T, 81.1 R, 89.1, 83.1
See application file for complete search history.

(56) References Cited

U.S. PATENT DOCUMENTS

| | | | |
|---|---|---|---|
| 5,839,137 A * | 11/1998 | Butler | A61G 1/01 5/89.1 |
| 5,896,859 A * | 4/1999 | Carroll | A61G 7/1023 128/845 |
| D418,301 S * | 1/2000 | Anderson | D3/327 |
| 6,073,280 A * | 6/2000 | Farnum | A62B 35/0025 5/89.1 |
| 6,357,551 B1 * | 3/2002 | Bogardus, III | E06C 1/56 182/196 |
| 7,585,197 B1 * | 9/2009 | Merten | E06C 1/56 182/189 |
| D666,896 S * | 9/2012 | Pinholster, Jr. | D8/356 |
| 8,321,972 B1 * | 12/2012 | Vetter | A61G 7/1023 5/81.1 R |
| 8,343,018 B2 * | 1/2013 | Moulton | A63B 23/035 482/131 |
| 8,944,976 B2 * | 2/2015 | Crowell | A63B 21/00043 482/121 |
| 9,003,579 B1 * | 4/2015 | Pinholster, Jr. | A45F 3/22 5/120 |
| 9,320,343 B1 * | 4/2016 | Pinholster, Jr. | A45F 3/22 |
| 9,622,566 B1 * | 4/2017 | Pinholster, Jr. | A45F 3/24 |
| 9,750,329 B1 * | 9/2017 | Pinholster, Jr. | A45F 3/24 |
| 9,907,389 B2 * | 3/2018 | Conlin | A45F 3/24 |
| 10,034,534 B1 * | 7/2018 | Pinholster, Jr. | A45F 3/24 |

(Continued)

FOREIGN PATENT DOCUMENTS

| | | | | |
|---|---|---|---|---|
| EP | 2522398 A1 * | 11/2012 | ........... | A61G 7/1023 |
| EP | 2522398 B1 * | 12/2014 | ........... | A61G 7/1023 |
| EP | 3903752 A1 * | 11/2021 | ............. | A61G 7/001 |

*Primary Examiner* — Robert G Santos
(74) *Attorney, Agent, or Firm* — Law Office of Robert M. Patino (57) ABSTRACT

A rescue strap is provided with a plurality of strap loops that wraps around the torso of a patient and is fed through one of the strap loops to make a girth hitch around the patient's torso. The rescue strap then wraps around the patient's upper legs and through another strap loop making another girth hitch to lift from the hips.

10 Claims, 10 Drawing Sheets

(56) References Cited

U.S. PATENT DOCUMENTS

| | | | |
|---|---|---|---|
| 10,292,485 B2* | 5/2019 | Conlin | D03D 3/005 |
| 10,897,983 B2* | 1/2021 | Conlin | D03D 11/02 |
| D911,152 S * | 2/2021 | Power, II | D8/356 |
| 10,918,194 B2* | 2/2021 | Conlin | D05B 93/00 |
| 11,000,110 B2* | 5/2021 | Conlin | D03D 11/02 |
| 11,026,417 B2* | 6/2021 | Power, II | A01M 31/02 |
| 2008/0132392 A1* | 6/2008 | Moulton | A63B 21/00043 |
| | | | 482/122 |
| 2013/0157821 A1* | 6/2013 | Crowell | A63B 21/4034 |
| | | | 482/129 |
| 2017/0127808 A1* | 5/2017 | Conlin | A45F 3/24 |
| 2018/0146769 A1* | 5/2018 | Conlin | D03D 1/00 |
| 2019/0174902 A1* | 6/2019 | Conlin | A45F 3/24 |
| 2019/0223581 A1* | 7/2019 | Conlin | D03D 11/02 |
| 2019/0298040 A1* | 10/2019 | Conlin | D03D 3/08 |
| 2021/0052452 A1* | 2/2021 | Rathke | D03D 1/0094 |
| 2021/0076666 A1* | 3/2021 | Power, II | F16B 2/08 |
| 2021/0244591 A1* | 8/2021 | Romang | A61G 7/1023 |
| 2021/0330531 A1* | 10/2021 | Wiggermann | A61G 7/001 |

* cited by examiner

RESCUE STRAP FOR CARRYING A PATIENT

BACKGROUND

In an emergency situation where a person, victim or patient (collectively referred to as "the patient" or "patients") needs to be rescued or moved, often a first responder or several first responders arrive on the scene with no tools to help a patient in need of movement. Such emergency situations might include incidents where the patient might be in harm's way, such as when there is a fire, flood or other emergency, and the patient needs to be moved promptly.

Furthermore, there are situations where the first responder is called to a non-emergency situation known as "Citizen Assist" situations. In these situations, sometimes a person or patient just needs assistance in getting to a standing or sitting position. This exercise is difficult when the person or patient is large and it is difficult to lift or support the person or patient without compromising the position of the first responder which can lead to mechanical injuries.

Currently firefighters and other first responders (collectively referred to as "rescuer" or "rescuers") resort to lifting very large patients by trying to lift a patient from behind with arms under their armpits. This position puts the rescuer at risk for back injury. This technique is difficult due to poor grip on patient and other rescuers being unable to assist in lifting. Large patients may have most of their weight in their hips and legs and a lift by their armpits is difficult. At times, this lift is painful for the patient.

As an alternative, some rescuers opt to roll a patient onto a tarp that has handles on the sides of it and then moving the tarp with the patient on the tarp out of the threatening zone and to a rescue vehicle. This mechanism requires a patient lying flat and rolling from one side to the other side to get the tarp underneath the patient. The patient is lifted in the lying down position. There are times when space does not allow for a patient to lie flat. Other times, the rolling action may not be easily performed.

Thus there is a need for a lifting mechanism that is lightweight and easily transportable on a rescuer. The lifting mechanism should be simple to use and operable by one or more rescuer. Furthermore, the lifting mechanism is should be useable when space is not conducive to rolling back and forth onto a tarp.

SUMMARY OF THE INVENTION

These shortcomings are addressed by the present invention referred to as a rescue strap. The invention pertains to aiding rescuers to effectively carry a patient in need of assistance. However, it can be appreciated that this rescue strap may be used by other operators that just want to move a patient for other means such as medical, entertainment, or recreational.

The present rescue strap addresses these above-mentioned problems by allowing the rescuer to easily carry the strap as the rescue strap bundles into a tight wad that can be folded into a carrying bag or tied into a bundle with another strap, string or rope. The rescue strap is designed to lift a patient from his torso and hips simultaneously. This design helps with the weight distribution and demands on the rescuer when lifting the patient.

In a first embodiment of the invention, the rescue strap has a lead end and a rear end. The rescue strap is comprised of a top strap made of a durable and flexible material and a bottom strap made of a durable and flexible material secured to the first strap by a plurality of stitch works.

The plurality of stitch works create a plurality of strap loops along a length of said bottom strap. Optionally, a center point marker may be located in a center region of the bottom strap or a center region of the top strap.

In a second embodiment of the invention, the rescue strap wraps around the torso of patient and is fed through one of the strap loops to create a secure connection around the patient's torso. Optionally, the rescue strap then wraps around the patient's upper legs and through other strap loops making another girth hitch to lift a patient up from the hips. This method allows rescuers to handle the patient such that will not slip off or require patient to assist rescuers with their own strength. Lifting from the torso and hips simultaneously puts the rescuers in good lifting form and provides adequate support to lift patient.

DETAILED DESCRIPTION

A rescue strap 10 as shown in FIGS. 1-7 illustrates the invention in a rolled out position; however, the rescue strap may be rolled or folded for storage or transport. In a preferred embodiment, the entire length of the rescue strap is 18 feet. This length is desirably big for a normal sized person because the extra length helps ensure that it would fit around someone slightly bigger in size. It may be appreciated that varying lengths between 8 feet to 25 feet would be acceptable for utility.

Figure 1:
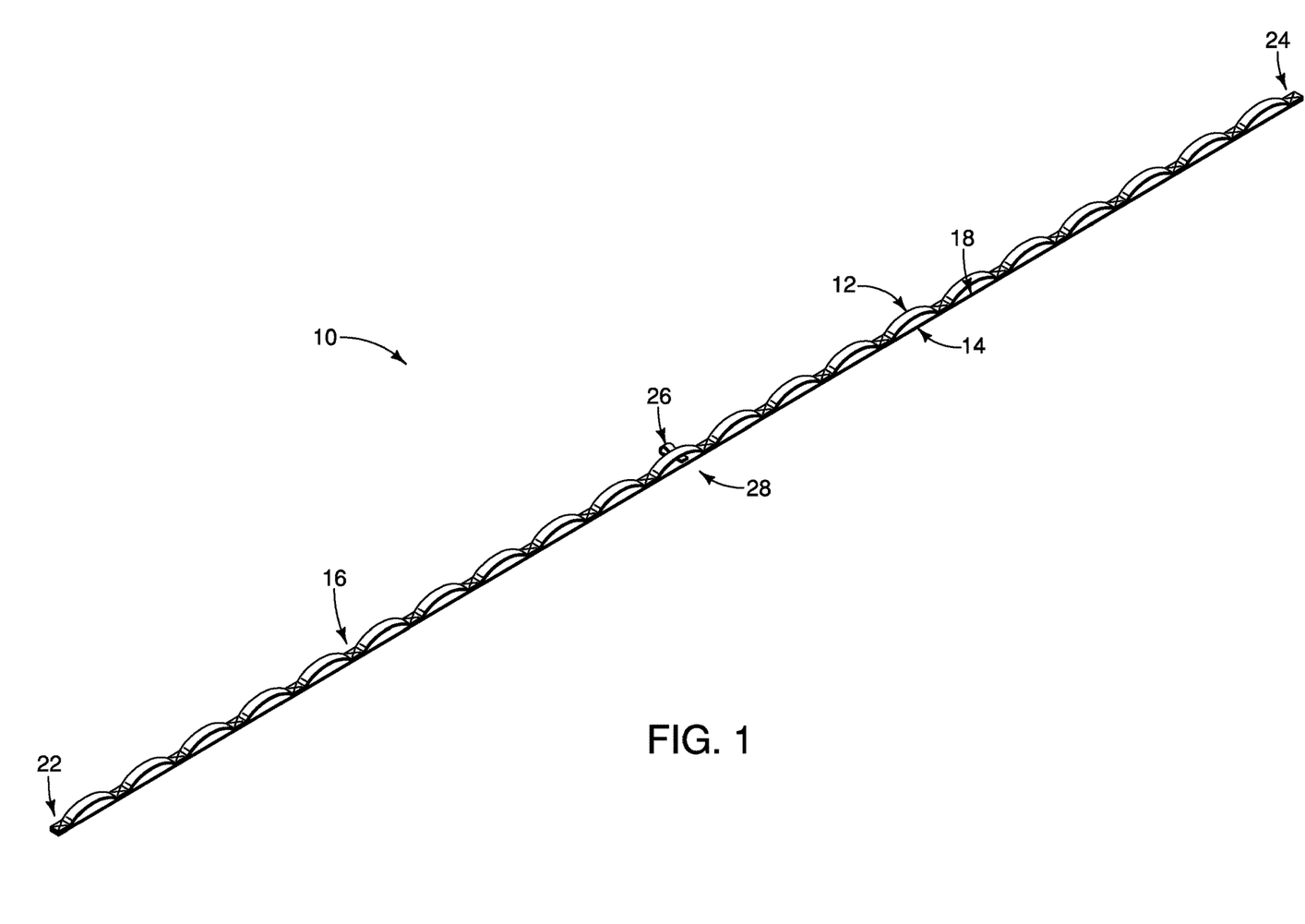
FIG. 1 is a top perspective view a rescue strap.
Figure 2:
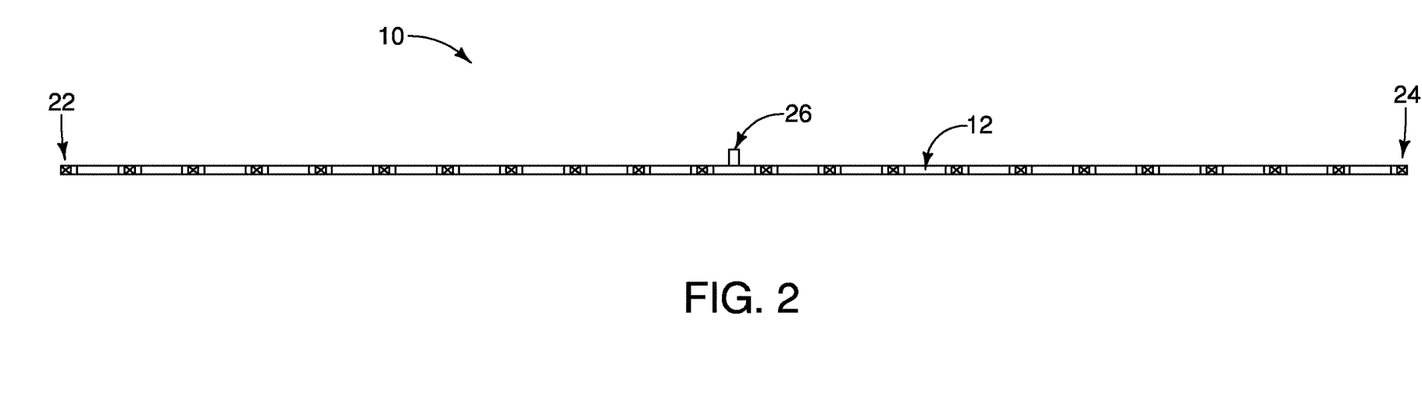
FIG. 2 is a top planar view of the rescue strap.
Figure 3:
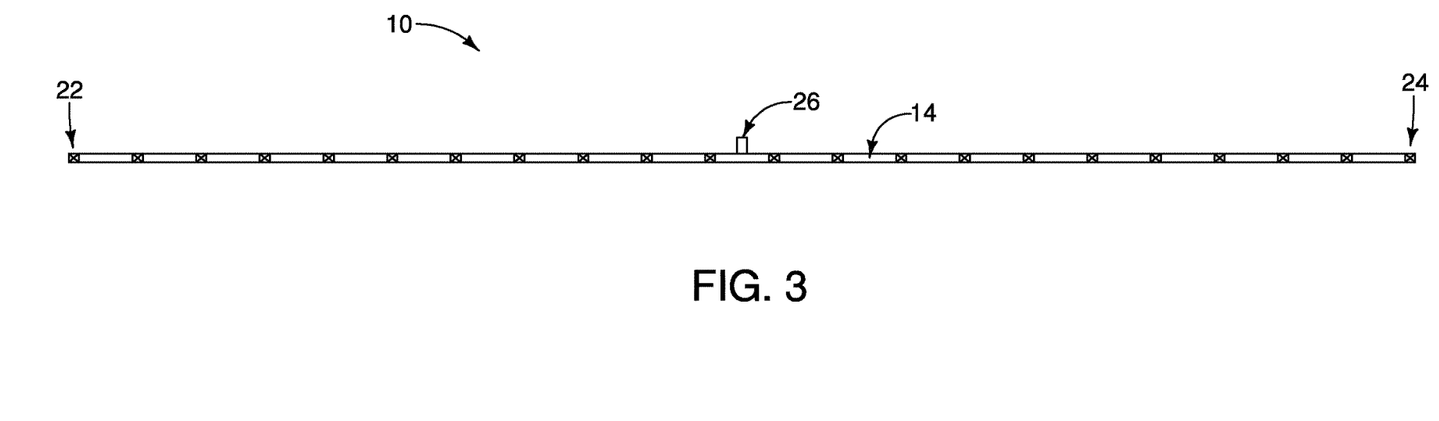
FIG. 3 is a bottom planar view of the rescue strap.
Figure 4:
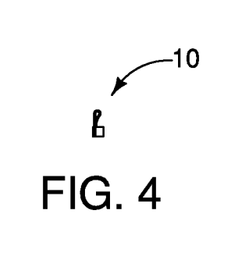
FIG. 4 is a front planar view of the rescue strap.
Figure 5:
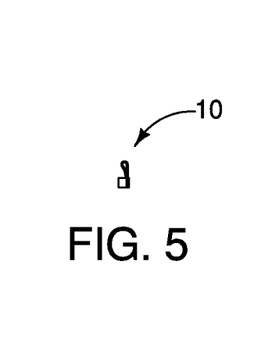
FIG. 5 is a rear planar view of the rescue strap.
Figure 6:
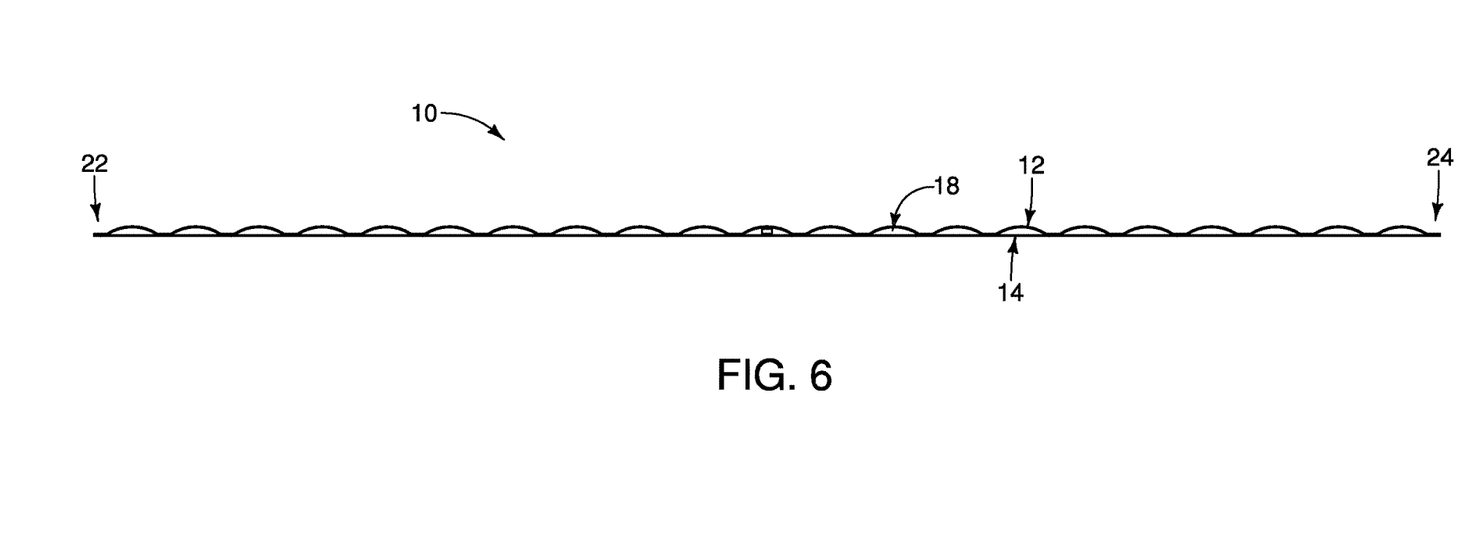
FIG. 6 is a left side planar view of the rescue strap.
Figure 7:
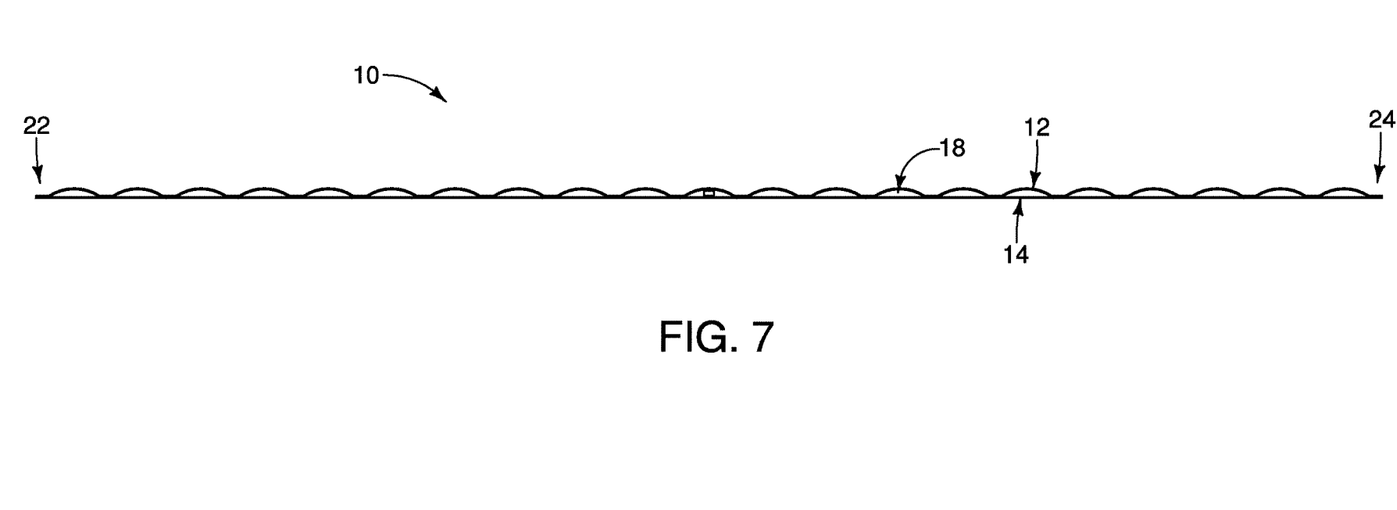
FIG. 7 is a right side planar view of the rescue strap.
Figure 8:
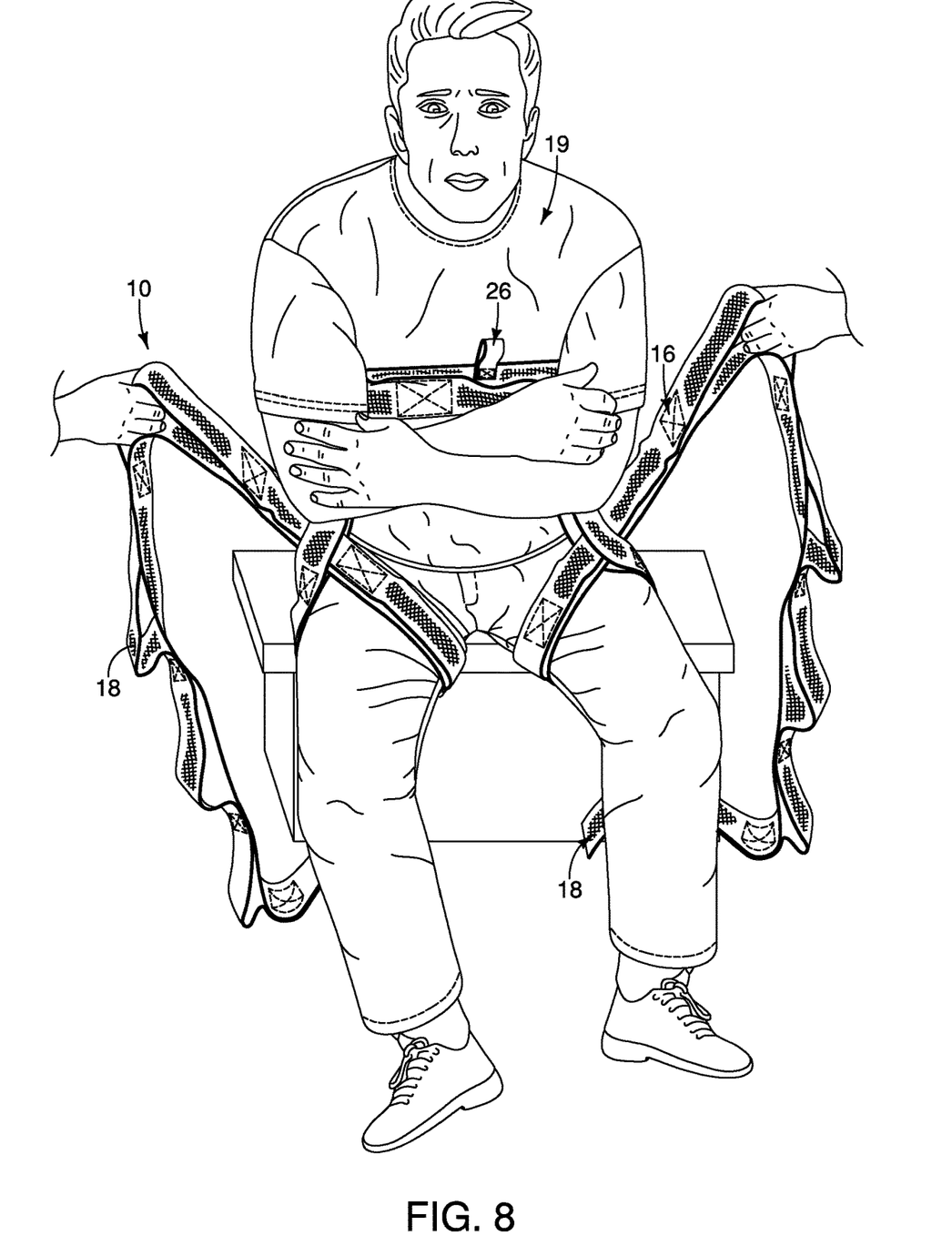
FIG. 8 is a front perspective view of a patient with the rescue strap wrapped around the patient.
Figure 9:
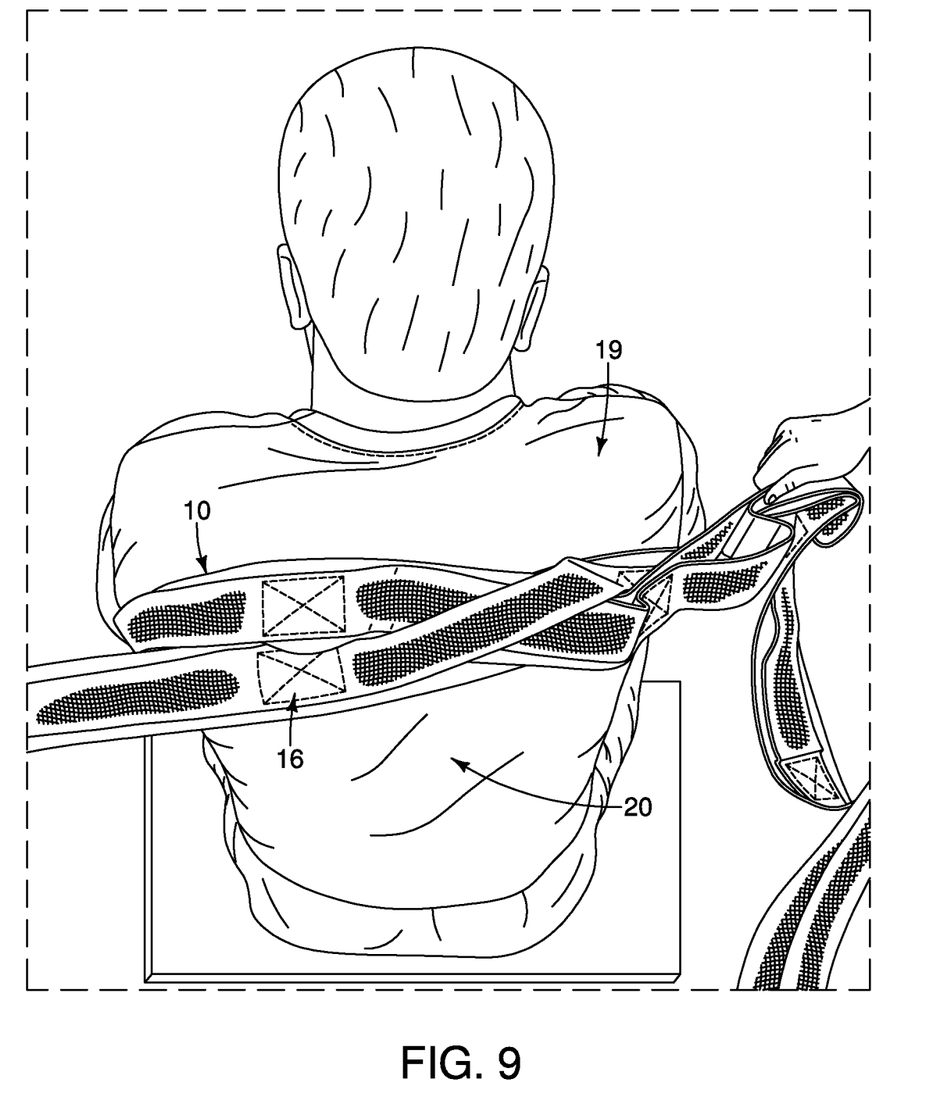
FIG. 9 is a rear perspective view of a patient with the rescue strap wrapped around the patient.

Now referring to FIGS. 1, 8 and 9, the rescue strap comprises of two straps, a top strap 12 and a bottom strap 14, stitched together at varying intervals via a plurality of stitch works 16. The top strap 12 and the bottom strap 14 are preferably made from a nylon webbing but other materials may also be used such as plastics, cotton, leather, or other durable, yet pliable material could be used. For the stitching, preferably the triple box X stitch is used which is well known in the field to give extra strength to the bond, but the triple bar stitch or other strong stitches could be used. The stitch works 16 should be made in approximately 4 to 12 inch intervals (or located 4 to 12 inches apart) to create a plurality of strap loops 18. More preferably, the stitch works 16 should be between 5 and 8 inch intervals such that a gloved hand could easily grasp the strap loop 18 as shown in FIG. 8. However, the stitch works 16 should not be so far apart that there is too much slack between stitching intervals to create an unstable grip or allow too much movement when a lead end 18 of the rescue strap 10 is fed within a strap loop 18 and the rescue strap moves too greatly from side to side in the strap loop. In a preferred embodiment, the plurality of stitch works 16 create a plurality of strap loops 18 along a length of the bottom strap 14 such that a strap loop 18 is present throughout the entire length the rescue strap 10.

Figure 10:
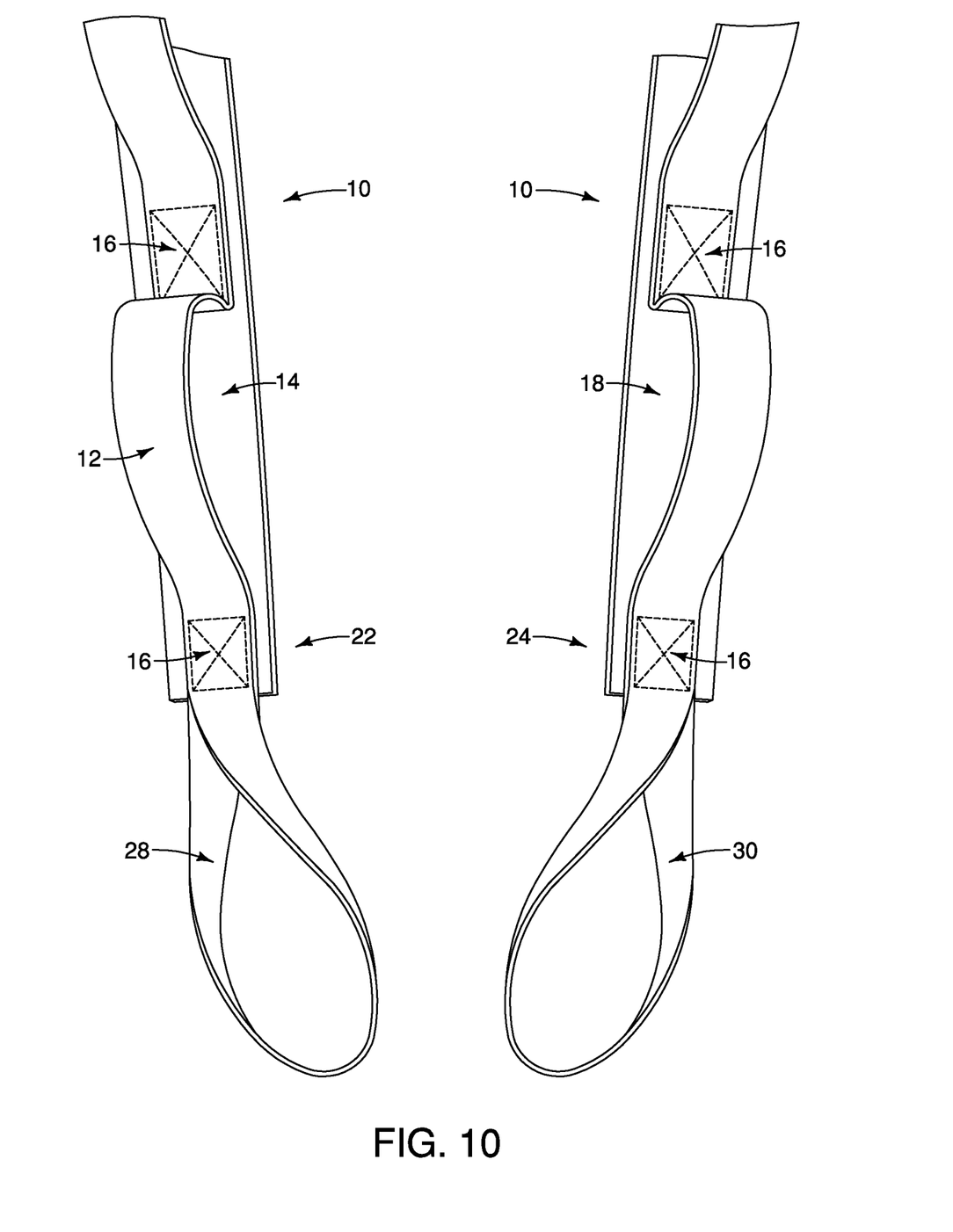
FIG. 10 is a close up view of a rear end and a lead end of the rescue strap with a first exterior handle and a second exterior handle.

To create the loop affect, the top strap 12 and the bottom strap 14 may be of substantially the same length in one embodiment. In another embodiment, the bottom strap 14 may be longer than the top strap 12 and when the stitches are made in consistent intervals, a bend is generated in the bottom strap 14. In the most preferred embodiment, the top strap 12 is longer than the bottom strap 14. In on embodiment using an 18 feet rescue strap 10, the bottom strap 14 is 18 feet long while the top strap 12 is 19 to 22 feet long. By stitching the top strap 12 every 8 inches for every 6 inches of the bottom strap 14, a natural bend in the top strap 12 is created that form the strap loops 18. The strap loops 18 are stitched one right after another create a continuous strap of handles or loops which provides sizing options depending on patient's size when feeding around patient s torso and legs. This design also provides many available handles for rescuers to lift from depending on the location of the patient 19 and rescuer. Now referring to FIG. 10, exterior handles are optionally provided on the end of the rescue strap 10 and are preferably in the shape of a loop. A first exterior handle 28 is provided on a lead end 22 of the rescue strap 10. A second exterior handle 30 is provided on a rear end 24 of the rescue strap 10.

In a preferred embodiment, the width of the top strap 12 and the bottom strap 14 differ to make it easier to grip the rescue strap 10 and feed the lead end 22 or rear end 24 of the rescue strap 10 through respective loops. To aid with the identification of the top strap 12 from the bottom strap 14 when in operation, the top strap 12 may be made of different color than that of the bottom strap 14. An optimal design will have the top strap 12 as being red and having a top strap width being the slightly less wide than the bottom strap 14. The bottom strap 14 in this embodiment will have a black strap being slightly wider than the top strap 12. The bottom strap is preferably about 3 inches wide, but could be between 1 and 6 inches wide. The top strap 12 is preferably about 2 inches wide and may vary in width in conjunction with the bottom strap 14. The top strap 12 can be the same width as the bottom strap; however, it is preferred that it is less wide so it can be easier to find the different straps and gripping it.

A center point marker 26 is preferably located in a center region 28 of the bottom strap 14 or in a center region 28 of the top strap 12. The center region 28 is generally defined as a region located in the central $\frac{1}{3}^{rd}$ section of the rescue strap 10 which applies to both the bottom strap 14 and the top strap 12, but is preferably more centrally located in the central $\frac{1}{10}^{th}$ section of the rescue strap 10. In a preferred embodiment, the center point marker 26 is a tag or small loop and is located at or near the center of the rescue strap 10. This center point marker 26 serves as a marker that a rescuer can pin near the center of a patient's chest or body when beginning the deployment of the rescue strap 12 on the patient 19. The center point marker 26 is preferably a simple off-colored fabric or durable material that is easily spotted and adhered through a stitch or glue to the rescue strap 12.

Now referring to FIG. 8 and FIG. 9, the rescue strap 10 does not require rolling of the patient 19 to apply. Nor does the rescue strap 10 require effort from the patient to use their legs or to keep their arms down. The patient 19 is lifted in a sitting position. This position makes it easier to move to a patient 19 to his bedside, chair, wheelchair, or stretcher. The rescue strap 10 was designed to lift a patient 19 from their torso and hips simultaneously. The rescue strap 10 wraps around the torso of the patient 19 while use the center point marker 26 to mark the center of the patient's chest. The lead end 22 of the rescue strap 10 is fed through one of the strap loops 18 to make a secure connection around a backside 20 of the patient's torso. The secure connection is preferably a hitch knot and more preferably a girth hitch. A rescuer then wraps the rescue strap 10 around the patient's upper legs and feeds the lead end 22 or the rear end 24 of the rescue strap 10 through another strap loop making another girth hitch to lift from the hips. Once the rescue strap 10 is locked around the patient's chest and legs as shown in FIGS. 8 and 9, multiple rescuers can help grab at different points. A minimum of one or two rescuers should be used but up to 6 rescuers could be used for a patient that is substantially difficult to lift or move. This design ensures that the rescuers are able to handle the patient 19 and that the patient 19 will not slip off. More importantly, this design does not require patient 19 to assist rescuers with his own strength. Furthermore, a rescuer lifting from his torso and hips simultaneously puts the rescuers in a good lifting form and provides adequate support to lift patient 19.

Figure 11:
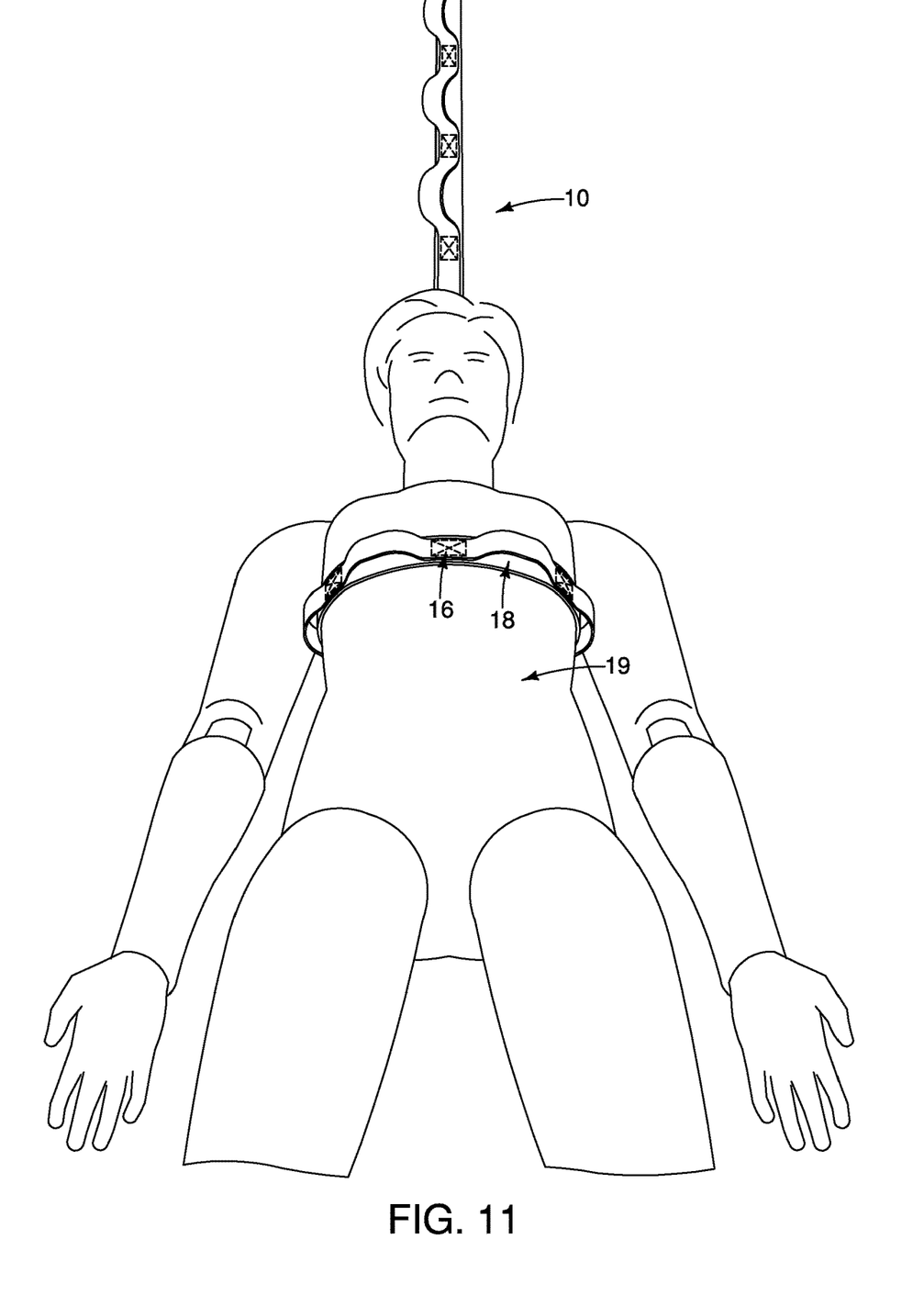
FIG. 11 is an optional method of wrapping the rescue strap around a torso of a patient.

Now referring to FIG. 11, in an optional embodiment, a different method may be employed to move a patient. A secure connection is still made on the backside 20 of a patient but the rear end 24 of the rescue strap 10 is fed through a strap loop 18 that is closer to the lead end 22. In this manner, the center point marker 26 is not located near the patient's chest, but rather the center point marker 26 resides behind the patient. A patient in this method embodiment is in a position to be dragged out on his back if that is what is required to transport the patient. This position is handy if there is only one rescuer available for moving the patient.

While a particular embodiment of the rescue strap has been described herein, it will be appreciated by those skilled in the art that changes and modifications may be made thereto without departing from the invention in its broader aspects and as set forth herein.

I claim:

1. A method of securing a patient in a strap with a torso and a right leg and a left leg in a rescue strap with a lead end and a rear end, comprising the steps of:
   wrapping a rescue strap around the torso of the patient, wherein said rescue strap with a lead end and a rear end is one continuous strap comprising:
   a top strap made of a durable and flexible material;
   a bottom strap made of a durable and flexible material secured to said top strap by a plurality of stitch works, whereby said plurality of stitch works create a plurality of strap loops along a length of said bottom strap; and
   a center point marker located in a center region of said bottom strap or a center region of said top strap,
   feeding the lead end of the rescue strap through a strap loop to make a secure connection around the torso,
   wrapping the lead end around the right leg of the patient and wrapping the rear end around the left leg of the patient, and
   inserting the lead end into a strap loop on an upper side of the right leg and inserting the rear end into a strap loop on an upper side of the left leg.

2. The method of claim 1, wherein said top strap and said bottom strap are the same length.

3. The method of claim 1, wherein said top strap is a greater length than said bottom strap.

4. The method of claim 3, wherein said stitch works reside every 4 to 12 inches apart.

5. The method of claim 4, wherein said top strap is less wide than the width of said bottom strap and said bottom strap is between 1 and 6 inches wide.

6. The method of claim 4, wherein said top strap is the same width of said bottom strap.

7. The method of claim 5, wherein said top strap is a different color than that of said bottom strap.

8. The method of claim 5, further comprising of a first exterior handle located on the lead end.

9. The method of claim 8, further comprising of a second exterior handle located on the rear end.

10. A method of securing a patient with a torso and a right leg and a left leg in a rescue strap with a lead end and a rear end, comprising the steps of:
   wrapping a rescue strap around the torso of the patient, wherein said rescue strap with a lead end and a rear end is one continuous strap comprising:
   a top strap made of a durable and flexible material;
   a bottom strap made of a durable and flexible material secured to said top strap by a plurality of stitch works, whereby said plurality of stitch works create a plurality of strap loops along a length of said bottom strap; and
   a center point marker located in a center region of said bottom strap or a center region of said top strap, and
   feeding the rear end of the rescue strap through a strap loop to make a secure connection around the torso.

\* \* \* \* \*